United States Patent

Wilk

[11] Patent Number: 5,192,266
[45] Date of Patent: Mar. 9, 1993

[54] DEVICE AND RELATED METHOD FOR REDUCING SWELLING OF HEMORRHOIDAL TISSUES

[76] Inventor: Peter J. Wilk, 185 W. End Ave., New York, N.Y. 10023

[21] Appl. No.: 919,058

[22] Filed: Jul. 23, 1992

Related U.S. Application Data

[63] Continuation-in-part of Ser. No. 837,069, Feb. 18, 1992.

[51] Int. Cl.$^5$ .............................................. A61M 31/00
[52] U.S. Cl. ....................................... 604/11; 604/54; 604/328
[58] Field of Search ............... 604/11, 27, 93, 285, 604/286, 288, 327, 328, 892.1, 891.1, 54; 128/898

[56] References Cited

U.S. PATENT DOCUMENTS

| | | | |
|---|---|---|---|
| 1,537,992 | 5/1925 | Gearon | 604/288 |
| 2,017,334 | 10/1935 | Ackerman | 604/285 |
| 3,760,804 | 9/1973 | Higuchi | 604/892.1 |
| 3,760,805 | 9/1973 | Higuchi | 604/892.1 |
| 3,929,132 | 12/1975 | Higuchi | 604/892.1 |
| 3,995,632 | 12/1976 | Nakano et al. | 604/892.1 |
| 4,563,182 | 1/1986 | Stoy et al. | 604/285 |
| 4,872,865 | 10/1989 | Bloebaum | 604/28 |

Primary Examiner—Randall L. Green
Assistant Examiner—Mary Beth O. Jones
Attorney, Agent, or Firm—R. Neil Sudol; Henry D. Coleman

[57] ABSTRACT

A method for treating hermorrhoids comprises the steps of (a) inserting a rectal probe or removable suppository through a rectal orifice, (b) drawing water from the hemorrhoidal tissues into the probe, (c) maintaining the probe disposed at least partially in the rectal orifice during the step of drawing, (d) expanding the probe during the step of drawing so that a portion of the probe remains in substantial direct contact with the hemorrhoidal tissues upon shrinkage of the hemorrhoidal tissues during the step of drawing, and (e) removing the probe from the rectal orifice upon sufficient shrinkage of the hemorrhoidal tissues. The probe carries a hypertonic or hydroscopic solution and is provided along an outer surface with an elastic semi-permeable membrane, whereby water diffuses osmotically through the membrane into the probe upon proper disposition thereof. The probe may also include an impermeable membrane which is deformable for enabling the formation of a reservoir to accommodate water which has been drawn into the probe from hemorrhoidal tissues.

8 Claims, 4 Drawing Sheets

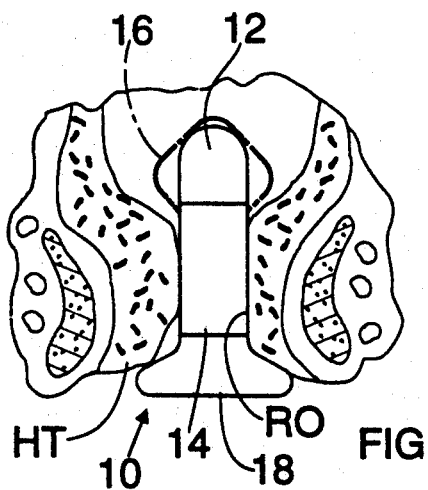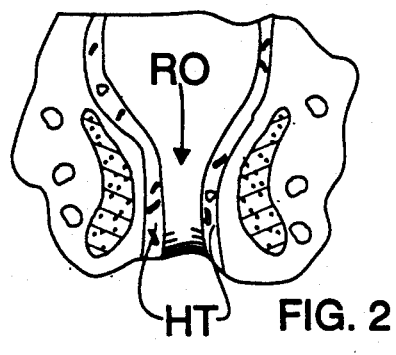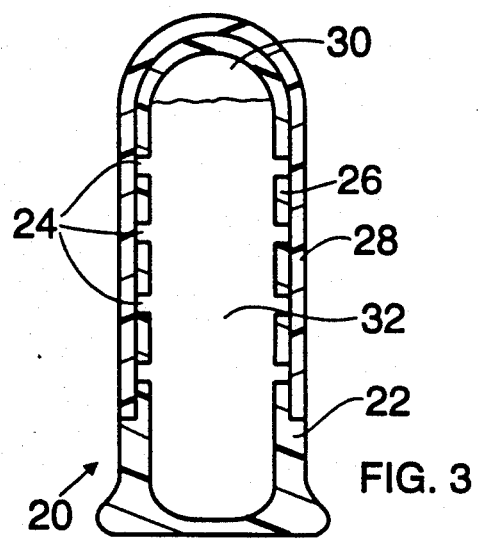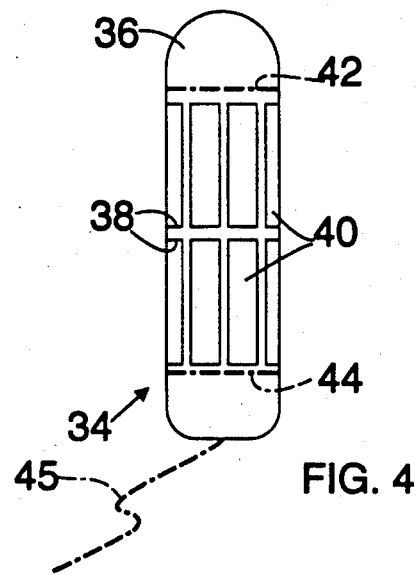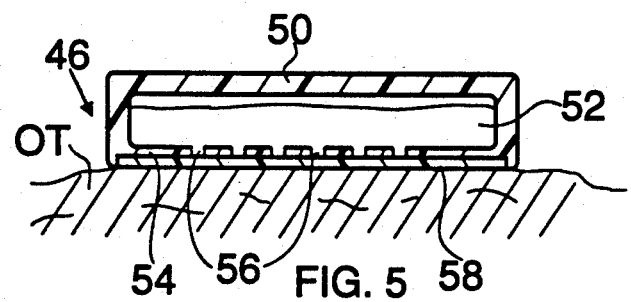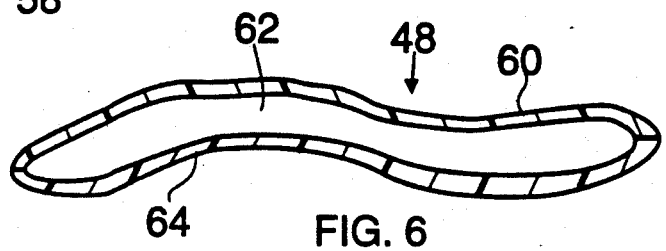

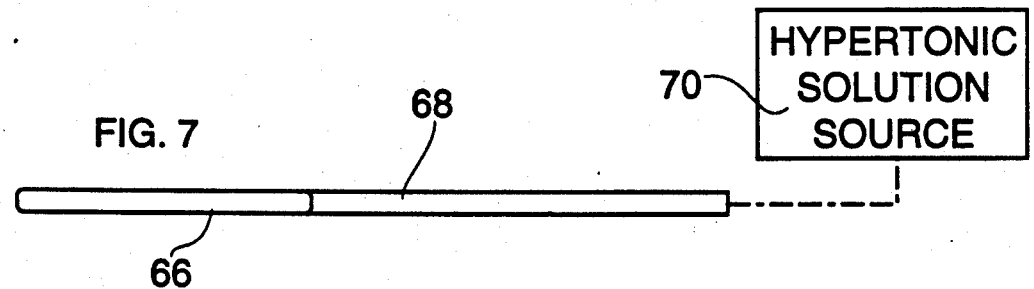
FIG. 7
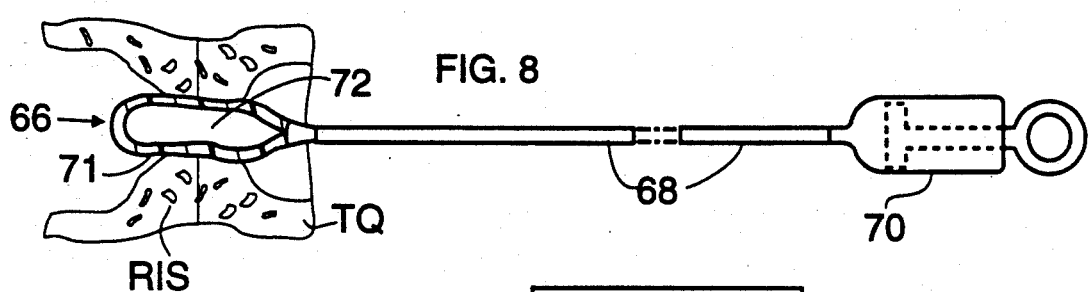
FIG. 8
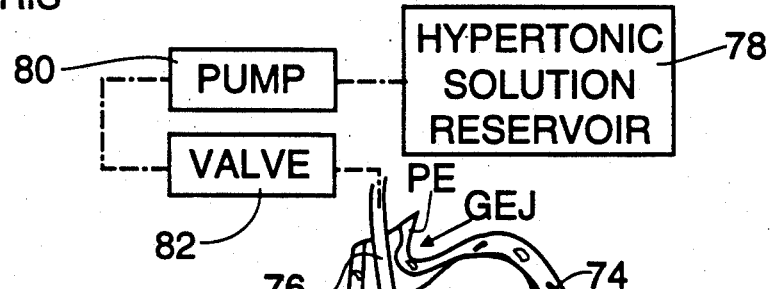
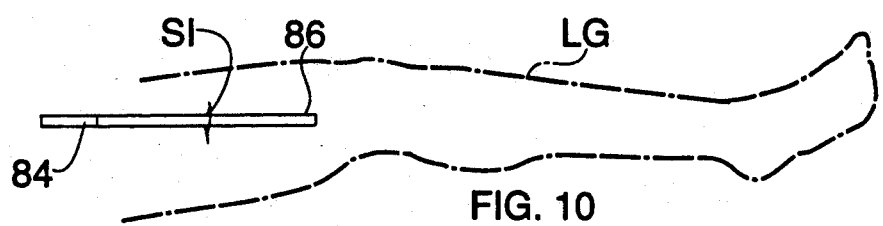
FIG. 9
FIG. 10

DEVICE AND RELATED METHOD FOR REDUCING SWELLING OF HEMORRHOIDAL TISSUES

CROSS REFERENCE TO A RELATED APPLICATION

This application is a continuation-in-part of copending application Ser. No. 837,069 filed Feb. 18, 1992.

BACKGROUND OF THE INVENTION

This invention relates to a device for reducing the swelling of hemorrhoidal tissues. This invention also relates to an associated method for reducing the swelling of hemorrhoidal tissues.

Hemorrhoids are a common malady which causes substantial pain and suffering to millions of people. The best conventional treatment for this affliction is a soaking of the hemorrhoidal tissues in a hypertonic bath, such as a solution of epsom salts. However, this treatment is not especially convenient for obvious reasons. A need exists for a more convenient and yet effective treatment for hemorrhoids.

OBJECTS OF THE INVENTION

An object of the present invention is to provide a device for treating swollen hemorrhoidal tissues.

A related object of the present invention is to provide an associated method for treating swollen hemorrhoidal tissues.

Another, more particular, object of the present invention is to provide such a device for treating hemorrhoids which is reusable.

These and other objects of the present invention will be apparent from the drawings and detailed descriptions herein.

SUMMARY OF THE INVENTION

A method for treating hemorrhoids comprises, in accordance with the present invention, the steps of (a) inserting a rectal probe or removable suppository through a rectal orifice, (b) drawing water from the hemorrhoidal tissues into the probe, (c) maintaining the probe disposed at least partially in the rectal orifice during the step of drawing, (d) expanding the probe during the step of drawing so that a portion of the probe remains in substantial direct contact with the hemorrhoidal tissues upon shrinkage of the hemorrhoidal tissues during the step of drawing, and (e) removing the probe from the rectal orifice upon sufficient shrinkage of the hemorrhoidal tissues.

Pursuant to another feature of the present invention, the probe contains a solution which is hypertonic or hydroscopic with respect to hemorrhoidal tissues. Accordingly, drawing of the water from the hemorrhoidal tissues into the probe is accomplished via osmotic pressure.

Pursuant to an additional feature of the present invention, the expansion of the probe is accomplished at least in part by forcing additional hypertonic solution into the probe. To that end the probe may be connected to a source of pressurized or pressurizable hypertonic fluid such as a collapsible bladder or pouch. A valve may be disposed between the pressurized or pressurizable source and the probe to control the direction of fluid flow at different stages during a hemorrhoidal treatment.

Where the probe includes an elastic semipermeable membrane along an outer surface of the probe, the expansion of the probe includes the step of deforming the membrane.

According to another feature of the present invention, the expansion of the probe is implemented automatically by the entry of water into the probe from the hemorrhoidal tissues.

An associated device for the treatment of hemorrhoids comprises, in accordance with the present invention, an expandable body member capable of being rectally inserted, a hypertonic or hydroscopic solution inside the body member, the solution being hypertonic with respect to hemorrhoidal tissues, and an elastic semipermeable membrane defining an outer surface of the body member and positioned along the body member so that the membrane deforms to enable an expansion of the body member upon a drawing of water from hemorrhoidal tissues through the membrane.

A method for treating hemorrhoids comprises, in accordance with another embodiment of the present invention, the steps of (i) inserting through a rectal orifice a rectal probe containing a solution which is hypertonic or hydroscopic with respect to hemorrhoidal tissues, (ii) drawing water from the hemorrhoidal tissues into the probe, (iii) maintaining the probe disposed at least partially in the rectal orifice during the drawing of the water from the hemorrhoidal tissues, (iv) extracting the probe from the rectal orifice upon sufficient shrinkage of the hemorrhoidal tissues, (v) removing diluted hypertonic solution from the probe upon the extraction of the probe, and (vi) placing new hypertonic solution into the probe, thereby preparing the probe for another use.

The removal of the diluted hypertonic solution from the probe may be accomplished by removing a plug from the probe to obtain access thereto.

A related device for the treatment of hemorrhoids comprises, in accordance with the present invention, a body member capable of being rectally inserted, a solution inside the body member which is hypertonic or hydroscopic with respect to hemorrhoidal tissues, and a semipermeable membrane defining a wall portion of the body member. The membrane is positioned along the body member so that the membrane is in contact with hemorrhoidal tissues upon insertion of the body member into a rectum. In addition, the body member is provided with a closable access port for obtaining access to the body member to replace diluted hypertonic solution in the body member with new hypertonic solution upon a use of the device.

A method for treating hemorrhoids comprises, in accordance with a further embodiment of the present invention, the steps of (1) inserting a rectal probe through a rectal orifice, (2) drawing water from the hemorrhoidal tissues into the probe, (3) maintaining the probe disposed at least partially in the rectal orifice during the step of drawing, (4) expanding a portion of the probe outside of the orifice during the step of drawing to form a reservoir of drawn off water, and (5) removing the probe from the rectal orifice upon sufficient shrinkage of the hemorrhoidal tissues.

According to another feature of the present invention, the probe includes an elastic membrane, the step of expanding including the step of deforming the membrane to form the reservoir.

A device for the treatment of hemorrhoids comprises, in accordance with the present invention, a body member capable of being rectally inserted, a hypertonic or hydroscopic solution inside the body member, the solution being hypertonic with respect to hemorrhoidal tissues, and a semipermeable membrane defining a wall portion of the body member, the membrane being positioned along the body member so that the membrane is in contact with hemorrhoidal tissues upon insertion of the body member into a rectum. The body member is provided in a base portion with an elastic membrane expandable outside of the orifice during the step of drawing to form a reservoir containing drawn off water.

The hypertonic or hydroscopic solution in a rectal probe in accordance with the present invention may contain any composition which will have the desired function. Magnesium sulfate (epsom salts) and sugar are suitable candidates.

A device for treating hemorrhoidal tissues in accordance with the present invention reduces swelling without the necessity for placing the patient in a bath. Accordingly, a method utilizing the device is convenient. For example, in treating hemorrhoids, the device may be used virtually anywhere. The device may be discarded upon use or re-used, in the event that an access port is provided.

BRIEF DESCRIPTION OF THE DRAWING

FIG. 1 is a side elevational view of a rectal probe in place inside a patient with hemorrhoids.

FIG. 2 is a schematic cross-sectional view of the rectal orifice in FIG. 1, showing reduction of hemorrhoidal swelling after use of a rectal probe in accordance with the present invention.

FIG. 3 is a schematic cross-sectional view of a rectal probe with a hypertonic or hydroscopic solution in accordance with the present invention.

FIG. 4 is a schematic side elevational view of another rectal probe.

FIG. 5 is a schematic cross-sectional view of a device for reducing the swelling of external organic tissues.

FIG. 6 is a schematic cross-sectional view of a similar device for reducing the swelling of external organic tissues.

FIG. 7 is partially a schematic side elevational view and partially a block diagram of a device for reducing the swelling of internal organic tissues, showing the device in a non-use configuration.

FIG. 8 is a schematic side elevational view of the device of FIG. 7, showing the device in a use configuration.

FIG. 9 is partially a schematic side elevational view and partially a block diagram of a device for reducing the swelling of internal organic tissues, particularly gastritis affected tissues, showing the device in a use configuration inside a stomach.

FIG. 10 is a schematic side elevational view of a device for reducing the swelling of traumatized muscle tissue.

DETAILED DESCRIPTION

Figure 11A:
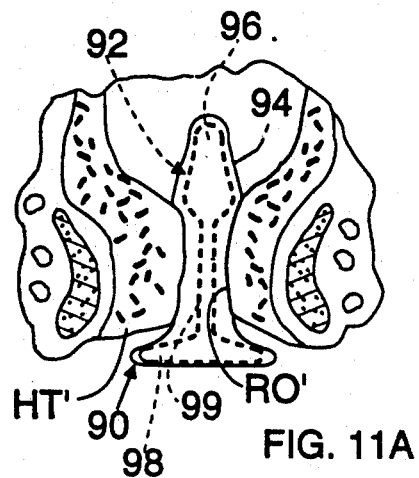
FIG. 11A is a side elevational view of a rectal probe in accordance with the present invention, showing the probe at the onset of a treatment procedure in place inside a patient with hemorrhoids.

As illustrated in FIG. 1, a rectal probe 10 is inserted into a rectal orifice RO afflicted by swollen hemorrhoidal tissues HT. Rectal probe 10 includes a body member 12 and at least one semipermeable membrane 14 disposed along an outer surface or wall of body member 12 so that the membrane is held in contact with the swollen hemorrhoidal tissues HT upon insertion of the probe into rectal orifice RO. Rectal probe 10 may be provided at a distal end with an enlarged head 16 serving to maintain the probe in rectal orifice RO during treatment of hemorrhoidal tissues HT. Rectal probe 10 may also be provided at a proximal end with a flange 18 which limits the penetration of the probe and which facilitates retrieval and removal thereof upon completion of a tissue reduction procedure.

Rectal probe 10 contains a hypertonic or hydroscopic solution, for example, a solution of magnesium sulfate or sugar. The hypertonic solution serves to draw water out of the swollen hemorrhoidal tissues HT through semipermeable membrane 14.

FIG. 2 illustrates reduction of the swelling of hemorrhoidal tissues HT after use of rectal probe 10.

As depicted in FIG. 3, a rectal probe 20 comprises a body member 22 provided along a central portion with an array of perforations 24. Disposed along an outer surface 26 of body member 22 is a semipermeable membrane 28. Body member 22 defines a central chamber 30 which carries a hypertonic or hydroscopic solution 32. The solution only partially fills chamber 30, in order to allow for the absorption of water during a treatment operation.

As illustrated in FIG. 4, another rectal probe 34 comprises a body member 36 provided along a central portion with a plurality of windows or apertures 38 each covered by a semipermeable membrane 40. Membrane 40 may be a unitary web, as indicated by dot-dash lines 42 and 44. Alternatively, windows 38 may be provided with respective semipermeable covers separate from each other. In any case, membrane 40 forms an outer wall or surface of body member 36 and engages swollen hemorrhoidal tissues (e.g., HT in FIGS. 1 and 2) upon disposition of rectal probe 34 in a treatment procedure.

Rectal probe 34 may in some cases take the form of a rectal suppository. In that case the probe remains in the rectal orifice until it is flushed out during a bowel movement. Alternatively, the probe may be provided with a string or other tensile element 45 for facilitating removal of the probe.

Probe 10 (FIG. 1) may also be used as a suppository. In that event, flange 18 is omitted and membrane 14 may extend around the entire body of the probe.

FIGS. 5 and 6 show respective devices 46 and 48 designed for reducing the swelling of external organic tissues OT. Device 46 comprises a rigid or semirigid body or casing member 50 containing a hypertonic solution 52 and provided along one wall 54 with an array of perforations 56. Disposed along an outer side of wall 54 is a semipermeable membrane 58. Device 46 is placed on swollen external organic tissues OT so that membrane 58 is in contact with those tissues.

Device 48 in FIG. 6 will be more appropriate for many uses. Device 48 comprises a body member or casing 60 made of a flexible, elastic material filled with a hypertonic or hydroscopic solution 62. A wall portion 64 of body member 60 is formed by a semipermeable membrane. Because body member 64 is flexible, it may be shaped to conform to the contour of swollen external tissues.

As illustrated in FIG. 7, a device for reducing the swelling of internal organic tissues, comprises a balloon 66 attached to the distal end of a tube 68 in turn connected at a proximal end to a source 70 of a hypertonic solution. Tube 68 is preferably made of a semirigid material, whereby tube 68 maintains its form but will flex to some extent under compressive pressure. Balloon 66 is made at least in part of a semipermeable membrane 71.

FIG. 8 shows balloon 66 and tube 68 inserted into an essentially tubular organ TO such as a urethra, an intestine or an esophagus. Balloon 66 has been juxtaposed to or aligned with a region of internal swelling RIS such as that occasioned by an anastomosis operation. Subsequently to the juxtaposition of balloon 66 and swelling RIS, a hypertonic or hydroscopic solution 72 has been fed or injected into balloon 66. To that end source 70 may take the form of a pump or a syringe 70, as illustrated in FIG. 8. Upon the elapse of a sufficient time to permit the reduction of swelling, source 70 is operated to withdraw hypertonic solution 72 from balloon 66 via tube 68. Balloon 66 and tube 68 are then extracted from the patient and discarded.

As illustrated in FIG. 9, another balloon 74 and tube 76 are inserted through a patient's esophagus PE into the stomach ST. Balloon 74 is made at least in part of a semipermeable membrane. Balloon 74 is inflated or expanded with a hypertonic or hydroscopic solution (not illustrated) which is fed or supplied from a reservoir 78 via a pump 80 and a valve 82 connected to tube 76. Subsequently to the inflation of balloon 74, tube 76 may be placed in tension to maintain the balloon in contact with swollen tissues in a gastritic region about the gastricesophageal junction GEJ.

It is to be noted that the devices of FIGS. 8 and 9 may be provided with pressure sensitive components (not shown) connected to tubes 68 and 76 for maintaining the hypertonic solution in balloons 66 and 74 at a substantially constant pressure or for automatically feeding increased amounts of hypertonic solution to balloons 66 and 74 as the swelling of the tissues is reduced. In that way, balloons 66 and 74 will maintain contact with the swollen tissues as the swelling subsides, thereby accelerating the treatment.

As illustrated in FIG. 10, a device for treating swollen muscle tissues, such as in a leg or thigh LG, comprises an elongate rod 84 carrying a hypertonic or hydroscopic solution (not illustrated) and provided along an external wall with a semipermeable membrane 86. Rod 84 is inserted through an incision SI made in the skin surface overlying or juxtaposed to the swollen muscle tissues of leg or thigh LG.

As illustrated in FIG. 11A, a rectal probe 90 is inserted into a rectal orifice RO' afflicted by swollen hemorrhoidal tissues HT, Rectal probe 90 includes a body or frame member 92 and at least one semipermeable membrane 94 surrounding the body member 92 so as to define an at least partially cylindrical outer surface or wall thereof. Body member 92 serves to support membrane 94 in an upright, elongated configuration and to enable or facilitate insertion of membrane 94 into rectal orifice RO' so that the membrane is held in contact with the swollen hemorrhoidal tissues HT' upon insertion of the probe into rectal orifice RO'. Body member 92 may be provided at a distal end with an enlarged head 96 serving to maintain the probe in rectal orifice RO' during treatment of hemorrhoidal tissues HT'. Body member 92 may also be provided at a proximal end with a flange 98 which limits the penetration of the probe and which facilitates retrieval and removal thereof upon completion of a tissue reduction procedure.

Figure 11B:
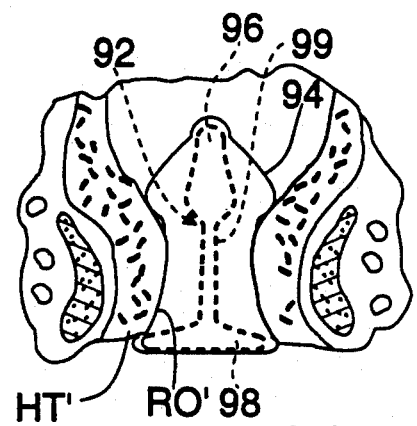
FIG. 11B is a view similar to FIG. 11A, showing the probe at a later stage of a treatment procedure in place inside a patient with hemorrhoids.

Membrane 94 is elastic and accordingly expands upon diffusion of water molecules through the membrane from hemorrhoidal tissues HT' after the probe has been inserted into orifice RO' during a treatment procedure, as illustrated in FIG. 11B. The expansion of membrane 94 and, accordingly, of probe 90 serves in part to maintain membrane 94 in substantial direct contact with swollen hemorrhoidal tissues HT, during the treatment, thereby enhancing the efficacy of the procedure.

Membrane 94 may be connected to body member 92 along head 96 and flange 98, thereby permitting expansion or inflation of the membrane about a central shaft 99 of body member 92.

Figure 12:
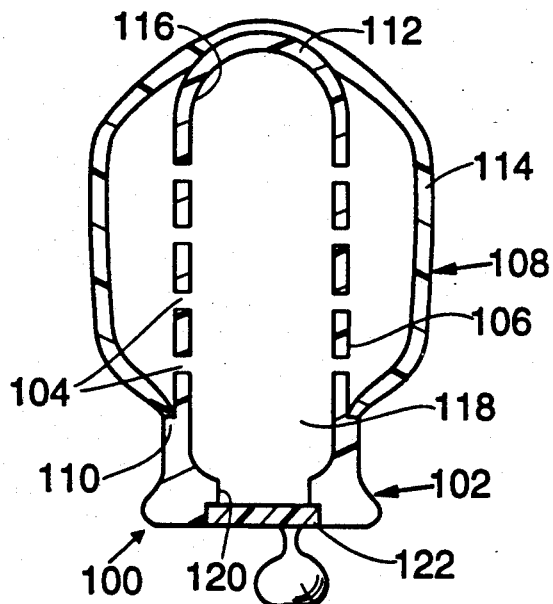
FIG. 12 is a schematic cross-sectional view of a rectal probe similar to the probe of FIG. 3, showing the probe with an expanded semi-permeable membrane after use of the probe to treat hemorrhoidal tissues.

As depicted in FIG. 12, a rectal probe 100 comprises a body member 102 provided along a central portion with an array of perforations 104. Disposed along an outer surface 106 of body member 102 is an elastic semipermeable membrane 108 connected to body member 102 at a base end 110 and a head 112 thereof. A cylindrical central portion 114 of membrane 108 is unattached to body member 102. Body member 102 defines a central chamber 116 which carries a hypertonic solution 118. Upon use of probe 100 in the treatment of hemorrhoids, membrane 108 and particularly central portion 114 thereof expands upon diffusion of water through the membrane from hemorrhoidal tissues.

As additionally depicted in FIG. 12, base 110 of probe 100 is provided with an access port 120 covered with a removable plug or door 122. Plug or door 122 may be provided with a knob 124 for facilitating removal of the plug upon the termination of a hemorrhoidal treatment. Upon extraction of probe 100 from a rectal orifice and upon removal of plug 122 from port 120, diluted hypertonic solution 118 is poured off. Probe 100 may then be refilled with fresh hypertonic solution in anticipation of a subsequent reuse of the device. Of course, membrane 108 collapses upon removal of plug 122 and again conforms to the outer surface 106.

FIG. 12 illustrates plug 122 as attachable in a force-lock fit to body member 102. However, other equivalent attachment techniques may be used, for example, a snap-lock fit (ridge and groove) or a screw-type connection.

Probes 10, 20, 34 and 90 may similarly be provided with closable access ports for enabling refilling and reuse of the probes.

Figure 13:
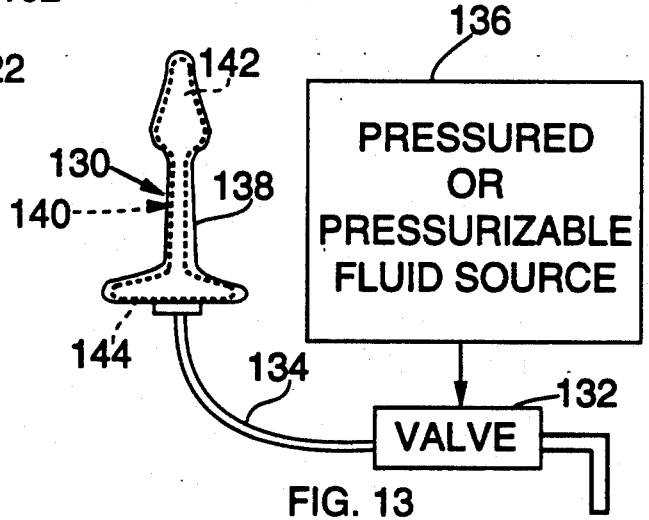
FIG. 13 is partially a schematic side elevational view and partially a block diagram of a device for treating hemorrhoids, in accordance with the present invention.

FIG. 13 shows a probe 130 wherein removal of diluted hypertonic or hydroscopic solution may be effectuated via a valve mechanism 132 connected via a hose 134 to the probe. Valve mechanism 132 is also connected to a pressurized or pressurizable source 136 of hypertonic solution. Source 136 may take the form of a collapsible bladder or pouch which is manually collapsible via a squeezing action. Valve mechanism 132 is disposed between source 136 and probe 130 to control the direction of fluid flow at different stages during a hemorrhoidal treatment.

Probe 130 includes an expandable or deformable semipermeable membrane 138 attached to an elongate support 140 having an enlarged head portion 142 at a distal end and a flange 144 at a proximal end.

During insertion or placement of probe 130 in a rectal orifice (not shown), membrane 138 is in a relatively collapsed or deflated configuration, as illustrated in FIG. 13, owing to a low fluid pressure. The relatively small size of probe 130 facilitates insertion of the probe and minimizes discomfort to the user. Upon insertion of probe 130, valve mechanism 132 is actuated to enable the transfer of hypertonic fluid from source 136 to probe 130. Valve mechanism 132 and/or source 136 is controlled by the user to maximize the pressure of the hypertonic solution inside probe 130, thereby maintaining maximal direct contact between hemorrhoidal tissues and semi-permeable membrane 138, without causing undue pain to the user. The user is thus able to balance the rate of water absorption against the pressure on the hemorrhoidal tissues by probe 130.

Upon absorption of water from the user's hemorrhoidal tissues, valve mechanism 132 may be actuated to drain diluted hypertonic solution from probe 130 and to refill the probe while the probe remains inserted in the user's rectal orifice. With that procedure, the effectiveness of hemorrhoidal treatment is enhanced inasmuch as a renewed high concentration of hypertonic solution draws water at a higher rate from the hemorrhoidal tissues. Upon termination of the treatment, valve mechanism 132 may be used to empty probe 130 of the diluted hypertonic solution prior to removal of probe 130 from the user's rectal orifice, thereby facilitating removal and reducing any pain which would otherwise be experienced during the removal process.

Valve mechanism 132 may take any suitable form. In a simple embodiment, hose 134 is bifurcated, with one branch extending to source 136 and another branch serving as an outlet, each branch being provided with a releasable clamp.

Figure 14A:
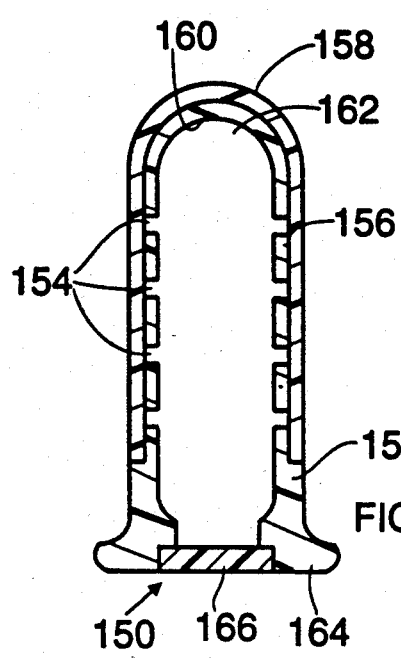
FIG. 14A is a schematic cross-sectional view, on a reduced scale, of another rectal probe in accordance with the present invention, showing the probe prior to use.
Figure 14B:
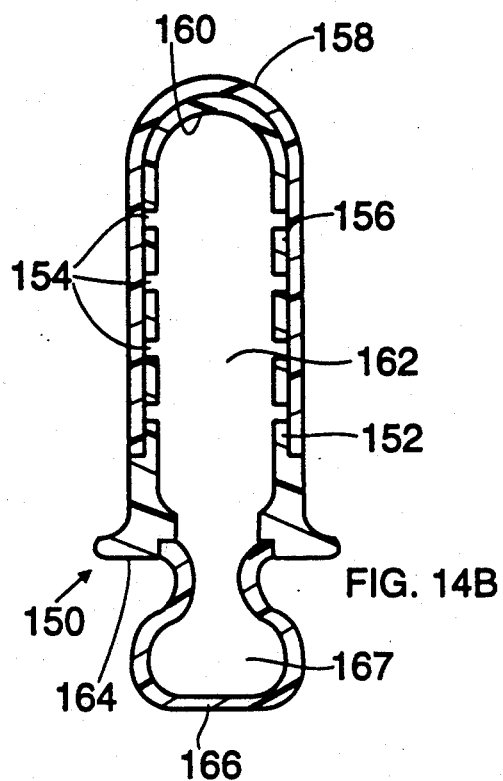
FIG. 14B is a view similar to FIG. 14A, showing the probe after use in treating hemorrhoidal tissues.

As shown in FIG. 14A, a rectal probe 150 comprises a body member 152 provided along a central portion with an array of perforations 154. Disposed along an outer surface 156 of body member 152 is a semipermeable membrane 158 connected to body member 152. Body member 152 defines a central chamber 160 which carries a hypertonic or hydroscopic solution 162. A base 164 of probe 150 is provided with an elastic impermeable membrane 166. Upon insertion of probe 150 into a user's rectum and consequent absorption of hemorrhoidal water, membrane 166 expands, as illustrated in FIG. 14B, to provide a reservoir 167 for the absorbed water.

Any probe or removable suppository for the treatment of hemorrhoidal tissues, as described herein, may be provided with a string 45 (FIG. 4) for facilitating removal of the device upon completion of treatment. In addition, the outer surface of the probe or suppository may be provided with a film of a local anesthetic or other medication prior to insertion, thereby providing immediate temporary relief.

Figure 15A:
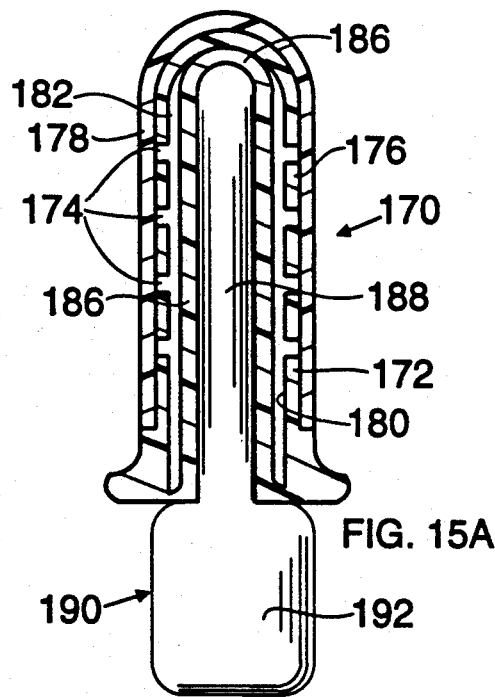
FIG. 15A is a schematic cross-sectional view of yet another rectal probe in accordance with the present invention, showing the probe ready for use.

As depicted in FIG. 15A, another rectal probe 170 comprises a body member 172 provided along a central portion with an array of perforations 174. Disposed along an outer surface 176 of body member 172 is a semipermeable membrane 178 connected to body member 172. Body member 172 defines a central chamber 180 which carries a hypertonic or hydroscopic solution 182. Probe 170 is hollow and is provided along an inner surface with an elastic impermeable membrane 186.

As further depicted in FIG. 15A, prior to use of the probe 170, an elongate inserter portion 188 of an applicator 190 is disposed inside membrane 186. Applicator 190 is used to insert probe 170 inside a user's rectal orifice. To that end applicator 190 is provided at a proximal end with a handle portion 192.

Figure 15B:
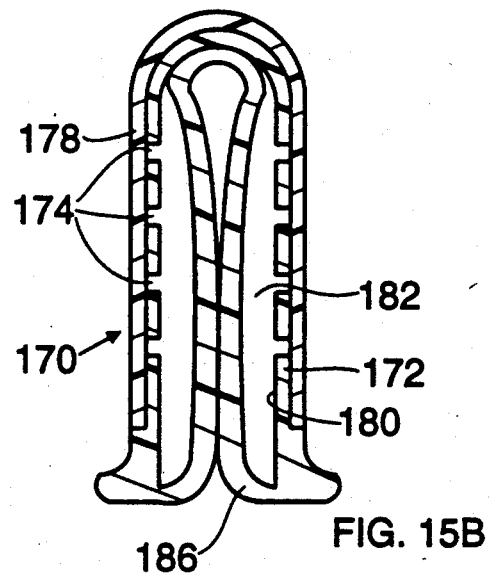
FIG. 15B is a view similar to FIG. 15A, showing the probe after use in treating hemorrhoidal tissues.

Upon insertion of probe 170 into a user's rectum, inserter portion 188 of applicator 190 is removed from the probe. Subsequent absorption of hemorrhoidal water causes membrane 186 to expand or deform inwardly, as illustrated in FIG. 15B, whereby chamber 180 increases in volume to provide a reservoir for the absorbed water. A string (not illustrated) may be attached to probe 170 to facilitate the removal thereof from a rectal orifice upon completion of the hemorrhoid treatment.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A method for treating hemorrhoids comprising the steps of:
   inserting a rectal probe through a rectal orifice;
   drawing water from the hemorrhoidal tissues into said probe;
   maintaining said probe disposed at least partially in the rectal orifice during said step of drawing;
   expanding said probe during said step of drawing so that a portion of said probe remains in substantial direct contact with the hemorrhoidal tissues upon shrinkage of the hemorrhoidal tissues during said step of drawing; and
   removing said probe from the rectal orifice upon sufficient shrinkage of the hemorrhoidal tissues.

2. The method defined in claim 1 wherein said probe contains a solution which is hypertonic with respect to hemorrhoidal tissues, said step of drawing being implemented via osmotic pressure.

3. The method defined in claim 1 wherein said probe includes an elastic semipermeable membrane along an outer surface of said probe, said step of expanding including the step of deforming said membrane.

4. The method defined in claim 1 wherein said step of expanding is implemented automatically by the entry of water into said probe from the hemorrhoidal tissues.

5. A device for the treatment of hemorrhoids, comprising:
an expandable body member capable of being rectally inserted;
a hypertonic solution inside said body member, said solution being hypertonic with respect to hemorrhoidal tissues; and
an elastic semipermeable membrane defining an outer surface of said body member and positioned along said body member so that said membrane deforms to enable an expansion of said body member upon a drawing of water from hemorrhoidal tissues through said membrane.

6. A method for treating hemorrhoids, comprising the steps of:
inserting through a rectal orifice a rectal probe containing a solution which is hypertonic with respect to hemorrhoidal tissues;
drawing water from the hemorrhoidal tissues into said probe;
maintaining said probe disposed at least partially in the rectal orifice during said step of drawing;
expanding an outer surface of said rectal probe during said step of drawing;
extracting said probe from the rectal orifice upon sufficient shrinkage of the hemorrhoidal tissues;
removing diluted hypertonic solution from said probe upon said step of extracting; and
placing new hypertonic solution into said probe, thereby preparing said probe for another use.

7. The method defined in claim 6 wherein said step of removing includes the step of removing a plug from said probe to obtain access thereto.

8. A device for the treatment of hemorrhoids, comprising:
a body member capable of being rectally inserted;
a solution inside said body member which is hypertonic with respect to hemorrhoidal tissues; and
an elastic semipermeable membrane defining an outer surface portion of said body member, said membrane being positioned along said body member so that said membrane is in contact with hemorrhoidal tissues upon insertion of said body member into a rectum,
said body member being provided with a closable access means for obtaining access to said body member to replace diluted hypertonic solution in said body member with new hypertonic solution upon a use of the device.

* * * * *